United States Patent
Fu et al.

(10) Patent No.: US 11,468,563 B2
(45) Date of Patent: Oct. 11, 2022

(54) COLON POLYP IMAGE PROCESSING METHOD AND APPARATUS, AND SYSTEM

(71) Applicant: TENCENT TECHNOLOGY (SHENZHEN) COMPANY LIMITED, Guangdong (CN)

(72) Inventors: Xinghui Fu, Shenzhen (CN); Zhongqian Sun, Shenzhen (CN); Hong Shang, Shenzhen (CN); Zijian Zhang, Shenzhen (CN); Wei Yang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 154 days.

(21) Appl. No.: 17/025,679

(22) Filed: Sep. 18, 2020

(65) Prior Publication Data

US 2021/0004959 A1    Jan. 7, 2021

Related U.S. Application Data

(63) Continuation of application No. PCT/CN2019/112788, filed on Oct. 23, 2019.

(30) Foreign Application Priority Data

Oct. 31, 2018 (CN) .......................... 201811287489.X

(51) Int. Cl.
  *G06T 7/00* (2017.01)
  *G06T 7/73* (2017.01)
  *G16H 30/40* (2018.01)

(52) U.S. Cl.
  CPC .............. *G06T 7/0012* (2013.01); *G06T 7/73* (2017.01); *G16H 30/40* (2018.01);
  (Continued)

(58) Field of Classification Search
  CPC ......... G06T 7/0012; G06T 2207/20081; G06T 2207/30016; G06T 2207/30096; G06T 2207/20084; G16H 30/40; G16H 50/20
  See application file for complete search history.

(56) References Cited

U.S. PATENT DOCUMENTS

| 7,572,284 B2 | 8/2009 | Abraham-Fuchs et al. |
| 2004/0264778 A1 | 12/2004 | Liang et al. |

(Continued)

FOREIGN PATENT DOCUMENTS

| CN | 1654011 | 8/2005 |
| CN | 1654011 | 2/2013 |

(Continued)

OTHER PUBLICATIONS

Zheng et al., "Localisation of Colorectal Polyps by Convolutional Neural Network Features Learnt from White Light and Narrow Band Endoscopic Images of Multiple Databases," 2018 40th Annual International Conference of the IEEE Engineering in Medicine and Biology Society (EMBC), 2018, pp. 4142-4145 (Year: 2018).*

(Continued)

*Primary Examiner* — Vu Le
*Assistant Examiner* — Julius Chai
(74) *Attorney, Agent, or Firm* — ArentFox Schiff LLP

(57) ABSTRACT

A colon polyp image processing method and apparatus and a system are disclosed in the embodiments of this application to detect a position of a polyp in real time and determine a property of the polyp, and thereby improve the processing efficiency of a polyp image. Embodiment of this application provide a colon polyp image processing method that can include detecting a position of a polyp in a to-be-processed endoscopic image by using a polyp positioning model, and positioning a polyp image block in the endoscopic image. The polyp image block can include a position region of the (Continued)

polyp in the endoscopic image. The method can further include performing a polyp type classification type on the polyp image block by using a polyp property identification model, and outputting an identification result.

20 Claims, 7 Drawing Sheets

(52) U.S. Cl.
CPC ............. *G06T 2207/10024* (2013.01); *G06T 2207/10068* (2013.01); *G06T 2207/20081* (2013.01); *G06T 2207/20084* (2013.01); *G06T 2207/30032* (2013.01)

(56) References Cited

U.S. PATENT DOCUMENTS

| | | | |
|---|---|---|---|
| 2005/0096712 | A1 | 5/2005 | Abraham-Fuchs et al. |
| 2011/0301447 | A1 | 12/2011 | Park et al. |
| 2018/0075599 | A1 | 3/2018 | Tajbakhsh et al. |
| 2018/0225820 | A1* | 8/2018 | Liang .................. G16H 50/20 |
| 2019/0268538 | A1 | 8/2019 | Shiratani |
| 2020/0074629 | A1* | 3/2020 | Zur .................. A61B 1/000096 |
| 2020/0135330 | A1* | 4/2020 | Sugie .................. G16H 50/20 |
| 2021/0113075 | A1* | 4/2021 | Ito .................. A61B 1/000094 |

FOREIGN PATENT DOCUMENTS

| | | |
|---|---|---|
| CN | 103315699 | 9/2013 |
| CN | 107240091 | 10/2017 |
| CN | 107730489 | 2/2018 |
| CN | 107895369 | 4/2018 |
| CN | 106934799 | 7/2018 |
| CN | 108292366 | 7/2018 |
| CN | 108596237 | 9/2018 |
| CN | 108615037 | 10/2018 |
| CN | 109447973 | 3/2019 |
| DE | 10346276 | 5/2005 |
| EP | 1522252 | 4/2005 |
| JP | 2018-515164 A | 6/2018 |
| WO | WO 2018/105062 A1 | 6/2018 |

OTHER PUBLICATIONS

Extended European Search Report issued in Chinese Patent Application No. 19878480.3 dated Nov. 30, 2021 (12 pages).
Pogorelov Konstantin, et al., "Efficient Disease Detection in Gastrointestinal Videos—Global Features Versus Neural Networks", Multimed Tools and Applications, Kluwer Academic Publishers, Boston, US vol. 76, No. 21; Jul. 19, 2017, pp. 22493-22525, (33 pages).
Zheng Yali, et al., "Localisation of Colorectal Polyps by Convolutional Neural Network Features Learnt from White Light and Narrow Band Endoscopic Images of Multiple Databases", 2018 40th Annual International Conference of the IEEE Engineering in Medicine and Biology Society (EMBC), IEEE, Jul. 18, 2018; pp. 4142-4145 (4 pages).
Office Action issued in Japanese Patent Application No. 2021-512995 dated Dec. 10, 2021 (with English translation) (6 pages).
International Search Report and Written Opinion dated Jan. 31, 2020 in International Application No. PCT/CN2019/112788, (6 pages).
Written Opinion dated Jan. 31, 2020 in International Application No. PCT/CN2019/112788. (4 pages).
Chinese Office Action dated Sep. 3, 2020 in Application No. 201811287489.X, (10 pages).

\* cited by examiner

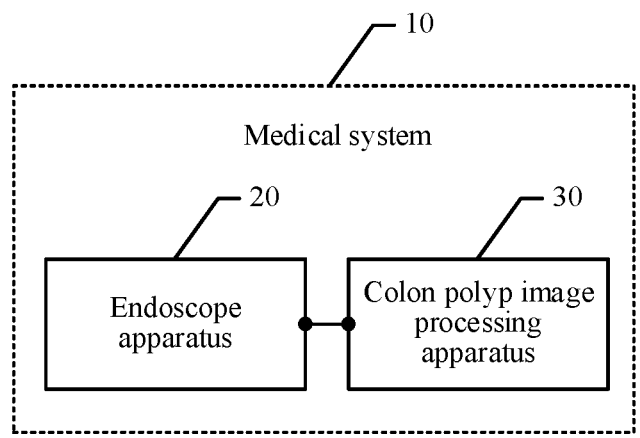

FIG. 1-a

| A colon polyp image processing apparatus detects a position of a polyp in a to-be-processed endoscopic image by using a polyp positioning model, and positions a polyp image block in the endoscopic image, where the polyp image block includes: a position region of the polyp in the endoscopic image | — 101 |

| The colon polyp image processing apparatus performs a polyp type classification detection on the polyp image block by using a polyp property identification model, and outputs an identification result | — 102 |

FIG. 1-b

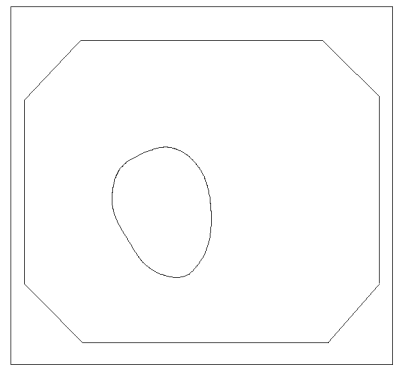
FIG. 6-a
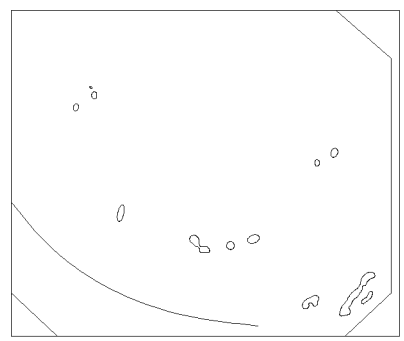
FIG. 6-b
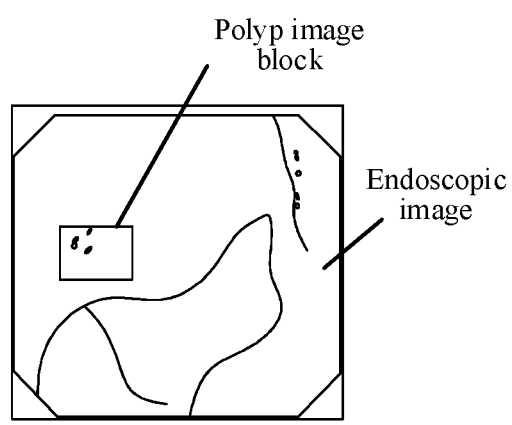
FIG. 7

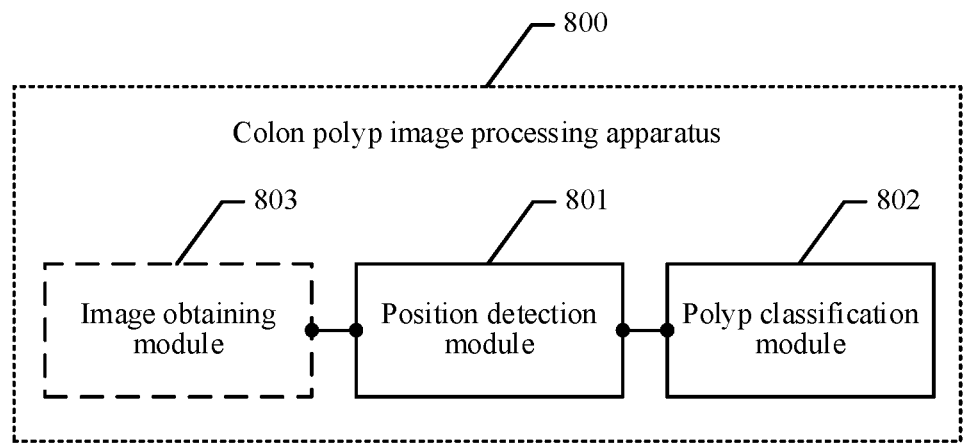
FIG. 8-a
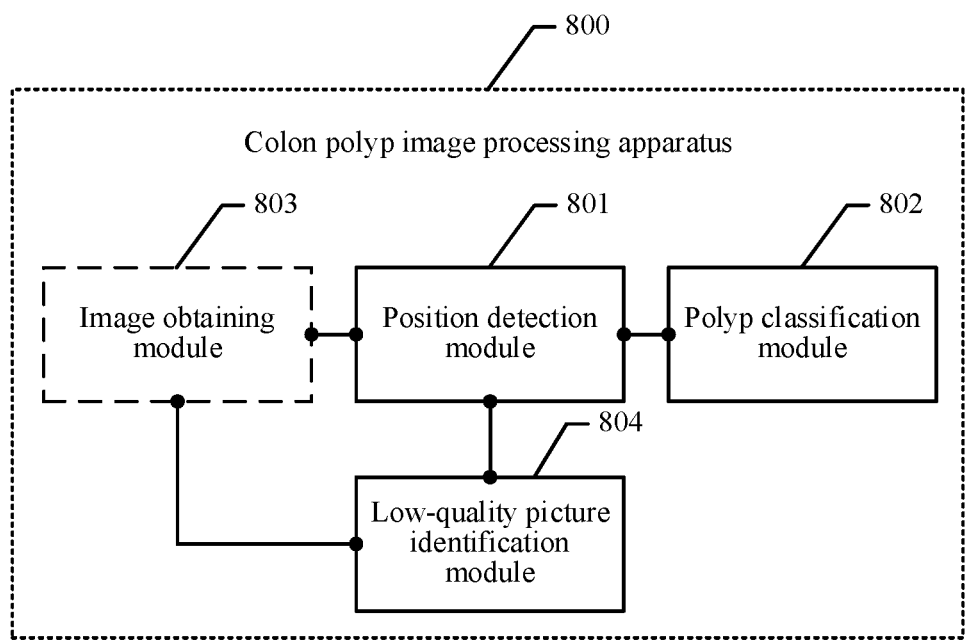
FIG. 8-b

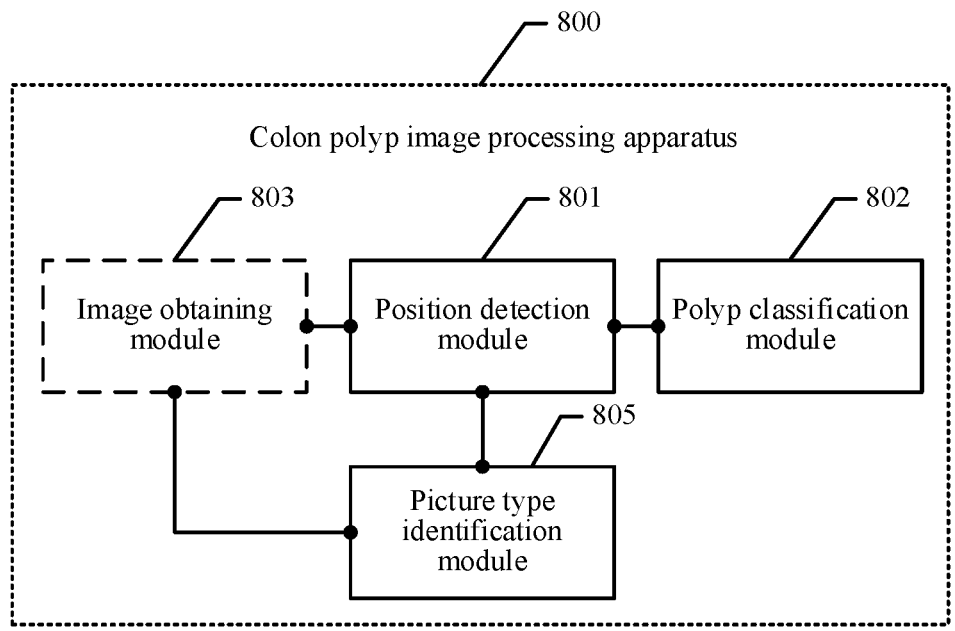
FIG. 8-c
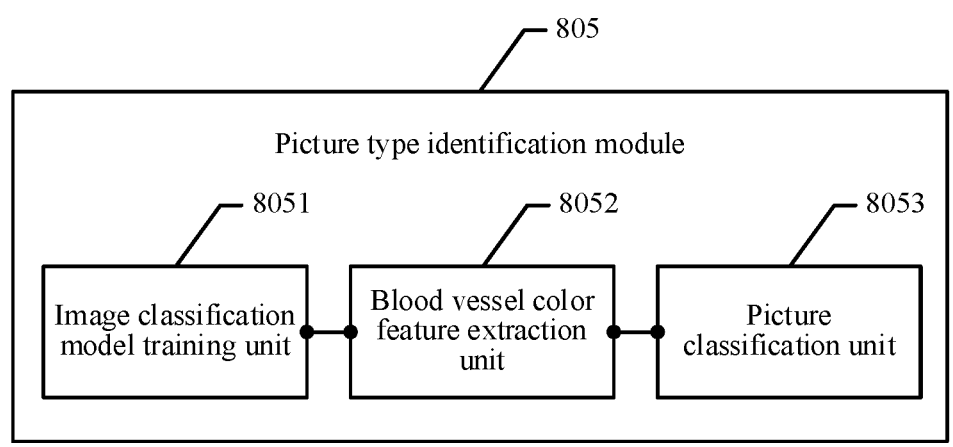
FIG. 8-d

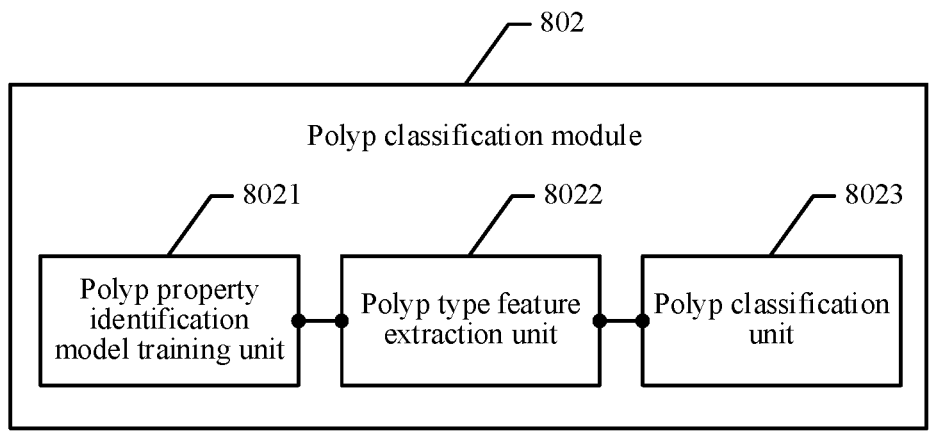
FIG. 8-e
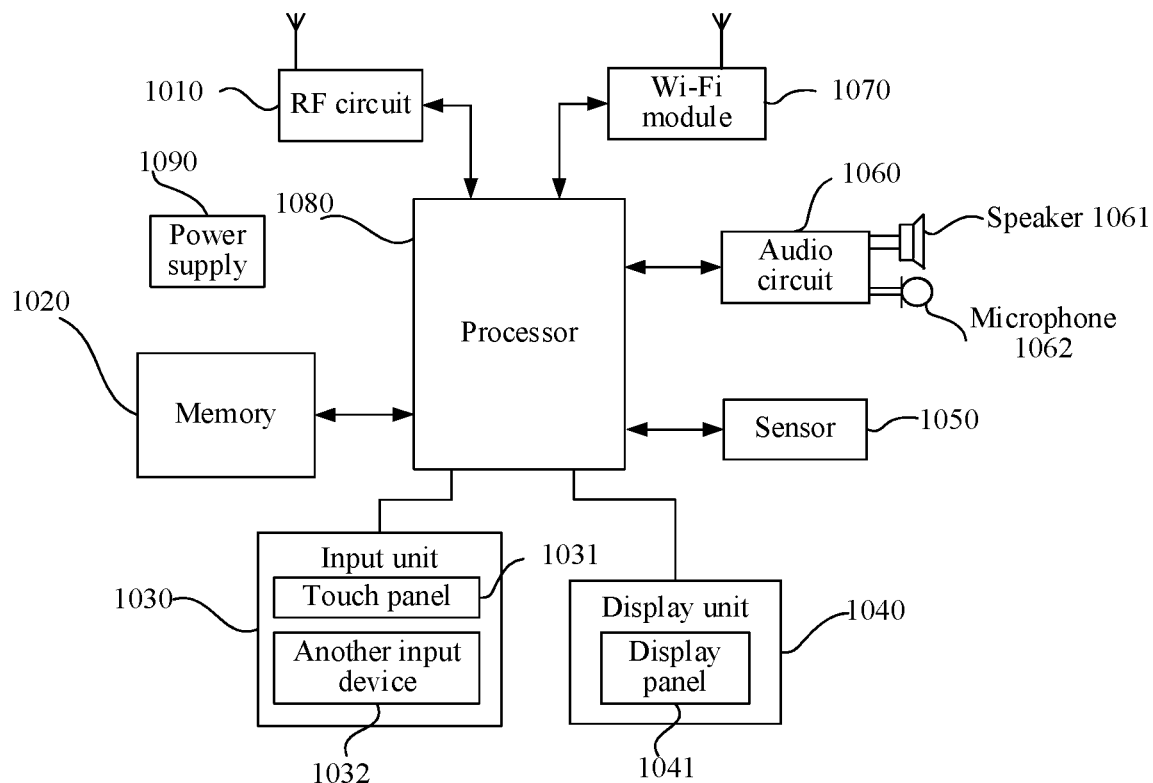
FIG. 9

COLON POLYP IMAGE PROCESSING METHOD AND APPARATUS, AND SYSTEM

RELATED APPLICATION

This application is a continuation of International Application No. PCT/CN2019/112788, filed on Oct. 23, 2019, which claims priority to Chinese Patent Application No. 201811287489.X, entitled "COLON POLYP IMAGE PROCESSING METHOD AND APPARATUS, AND SYSTEM" filed on Oct. 31, 2018. The entire disclosures of the prior applications are hereby incorporated by reference in their entirety.

FIELD OF THE TECHNOLOGY

Embodiments of this application relate to the field of computer technologies, including a colon polyp image processing method and apparatus, and a system.

BACKGROUND OF THE DISCLOSURE

At present, the colon cancer ranks in the top five among high-occurrence malignant tumors in China, and the incidence of the colon cancer in North America and Europe is also high. Colon cancer is a malignant digestive tract tumor that often occurs in the colon. Generally speaking, 50% of patients with advanced colon cancer die of recurrence and metastasis, and nearly 100% of patients with early colon cancer may be completely cured. Therefore, it is necessary to prevent and cure colon cancer. However, the early colon cancer cannot be predicted by clinical symptoms.

In the related art, when identifying colon polyps, a method of sliding window is usually used for detecting a polyp image. The sliding window means sliding an image block from top to bottom first and then from left to right in an endoscopic video image frame. The position of the polyp is manually marked. After the position of the polyp is determined, by using a computer vision extraction method, an identification result is outputted through classification.

In the sliding window method, it is calculated whether every image block includes a polyp by using a sliding window in an endoscopic video image frame. Due to a large amount of image blocks, the amount of calculation is large and the real-time performance cannot meet requirements. When the endoscope is controlled to move, an identification result of an image acquired in real time cannot be outputted in real time. The real-time performance of the manual marking method cannot meet requirements. When the endoscope is controlled to move, an identification result of an image acquired in real time cannot be outputted in real time.

SUMMARY

Embodiments of this application provide a colon polyp image processing method and apparatus, and a system, to detect a position of a polyp in real time and determine a property of the polyp, thereby improving the processing efficiency of a polyp image.

According to one aspect, an embodiment of this application provides a colon polyp image processing method. The method can include detecting, by a colon polyp image processing apparatus, a position of a polyp in a to-be-processed endoscopic image by using a polyp positioning model, and positioning a polyp image block in the endoscopic image, the polyp image block a position region of the polyp in the endoscopic image. The method can further include performing, by the colon polyp image processing apparatus, a polyp type classification detection on the polyp image block by using a polyp property identification model, and outputting an identification result.

According to another aspect, an embodiment of this application further provides a colon polyp image processing apparatus. The apparatus can include processing circuitry that is configured to detect a position of a polyp in a to-be-processed endoscopic image by using a polyp positioning model, and position a polyp image block in the endoscopic image, the polyp image block including: a position region of the polyp in the endoscopic image. The processing circuitry can be further configured to perform a polyp type classification detection on the polyp image block by using a polyp property identification model, and output an identification result.

In the foregoing aspect, the composition modules of the colon polyp image processing apparatus may further perform steps described in the foregoing aspect and various possible implementations. For details, refer to the foregoing descriptions of the foregoing aspect and various possible implementations.

According to another aspect, an embodiment of this application further provides a medical system, including an endoscope apparatus and a colon polyp image processing apparatus, a communication connection being established between the endoscope apparatus and the colon polyp image processing apparatus. The endoscope apparatus being configured to generate an endoscopic video stream, and transmit the generated endoscopic video stream to the colon polyp image processing apparatus. The colon polyp image processing apparatus can be configured to receive the endoscopic video stream from the endoscope apparatus, obtain a to-be-processed endoscopic image from the endoscopic video stream, detect a position of a polyp in a to-be-processed endoscopic image by using a polyp positioning model, and position a polyp image block in the endoscopic image. The polyp image block can include a position region of the polyp in the endoscopic image. The apparatus can further be configured to perform polyp type classification detection on the polyp image block by using a polyp property identification model, and output an identification result.

An embodiment of this application provides an image processing method. The method can include detecting, by an image processing apparatus, a position of a target object in a to-be-processed image by using a target object positioning model, and positioning a target object image block in the image, the target object image block including: a position region of the target object in the image. The method can further include performing, by the image processing apparatus, a target object type classification detection on the target object image block by using a target object property identification model, and outputting an identification result.

According to another aspect, an embodiment of this application provides a colon polyp image processing apparatus. The apparatus can include a processor and a memory. The memory can be configured to store an instruction, and the processor being configured to execute the instruction in the memory, to cause the colon polyp image processing apparatus to perform the method according to any one of the foregoing aspects.

Further, an embodiment of this application can provide a non-transitory computer-readable storage medium. The computer-readable storage medium storing an instruction that, when run on a computer, causes the computer to perform the method according to the foregoing aspects.

In an embodiment of this application, a position of a polyp in an endoscopic image is detected by using a polyp positioning model first, and a polyp image block is positioned in the endoscopic image. The polyp image block includes a position region of the polyp in the endoscopic image. Finally, a polyp type classification detection is performed on the polyp image block by using a polyp property identification model, and an identification result is outputted. In the embodiments of this application, because the position of the polyp is detected by using the polyp positioning model, the polyp image block may be directly positioned in the endoscopic image. The classification detection for the polyp type is also performed on the polyp image block, and does not need to be performed on the entire endoscopic image. Therefore, the real-time performance meets requirements. When the endoscope is controlled to move, an identification result of an image acquired in real time can be outputted in real time, thereby improving processing efficiency of the polyp image.

BRIEF DESCRIPTION OF THE DRAWINGS

To describe the technical solutions in the exemplary embodiments of this application more clearly, the following briefly introduces the accompanying drawings required for describing the embodiments. The accompanying drawings in the following description show only some exemplary embodiments of this application, and a person skilled in the art may still derive other accompanying drawings from the accompanying drawings.

FIG. 1-*a* is a schematic structural diagram of compositions of a medical system according to an embodiment of this application.

FIG. 1-*b* is a schematic block flowchart of a colon polyp image processing method according to an embodiment of this application.

FIG. 6-*a* is a schematic diagram of an endoscopic image that is a white light type picture according to an embodiment of this application.

FIG. 6-*b* is a schematic diagram of an endoscopic image that is a narrow band imaging (NBI) type picture according to an embodiment of this application.

FIG. 7 is a schematic diagram of a polyp image block circled on an endoscopic image according to an embodiment of this application.

FIG. 8-*a* is a schematic structural diagram of compositions of a colon polyp image processing apparatus according to an embodiment of this application.

FIG. 8-*b* is another schematic structural diagram of compositions of a colon polyp image processing apparatus according to an embodiment of this application.

FIG. 8-*c* is another schematic structural diagram of compositions of a colon polyp image processing apparatus according to an embodiment of this application.

FIG. 8-*d* is a schematic structural diagram of composition of a picture type identification module according to an embodiment of this application.

FIG. 8-*e* is a schematic structural diagram of compositions of a polyp classification module according to an embodiment of this application.

FIG. 9 is a schematic structural diagram of compositions of a terminal to which a colon polyp image processing method is applied according to an embodiment of this application.

DESCRIPTION OF EMBODIMENTS

Figure 2:
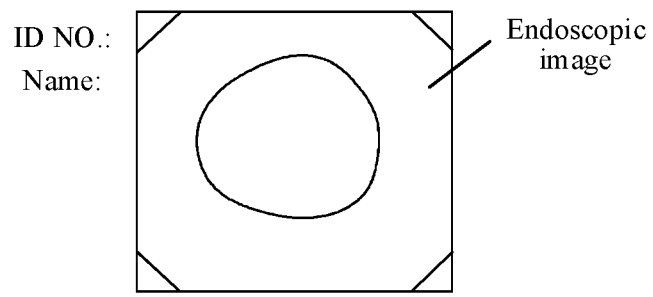
FIG. 2 is a schematic diagram of an endoscopic image according to an embodiment of this application.

Exemplary embodiments of this application provide a colon polyp image processing method and apparatus, and a system, to detect a position of a polyp in real time and determine a property of the polyp, thereby improving the processing efficiency of a polyp image.

To make the inventive objectives, features, and advantages of the embodiments of this application clear and comprehensible, the following clearly describes the technical solutions in the exemplary embodiments of this application with reference to the accompanying drawings in the embodiments of this application. The embodiments described below are merely some rather than all of the embodiments of this application. All other embodiments obtained by a person skilled in the art based on the embodiments of this application shall fall within the protection scope of this application.

In the specification, the claims, and the foregoing accompanying drawings of this application, the terms "include", "have", and any other variations are meant to cover the non-exclusive inclusion, so that a process, method, system, product, or device that includes a list of units is not necessarily limited to those listed units, but may include other units not expressly listed or inherent to such a process, method, product, or device.

An embodiment of the colon polyp image processing method in this application may be specifically applied to a scene of processing a colon polyp image in an endoscopic video stream. An identification result may be output after the colon polyp image is processed according to this embodiment of this application. The identification result may be used for helping a doctor discover a polyp in real time and determine a property of the polyp during an endoscopic examination, and guiding the doctor to perform a next operation.

An embodiment of this application further provides a medical system. As shown in FIG. 1-*a*, the medical system 10 can include an endoscope apparatus 20 and a colon polyp image processing apparatus 30. Further, a communication connection can be established between the endoscope apparatus 20 and the colon polyp image processing apparatus 30. The endoscope apparatus 20 is configured to generate an endoscopic video stream and transmit the generated endoscopic video stream to the colon polyp image processing apparatus 30.

The colon polyp image processing apparatus 30 is configured to receive the endoscopic video stream from the endoscope apparatus 20, obtain a to-be-processed endoscopic image from the endoscopic video stream, detect a position of a polyp in the to-be-processed endoscopic image by using a polyp positioning model, and position a polyp image block in the endoscopic image. The polyp image block includes a position region of the polyp in the endoscopic image. The colon polyp image processing apparatus 30 can further perform a polyp type classification detection on the polyp image block by using a polyp property identification model, and output an identification result.

The medical system provided by this embodiment of this application includes an endoscope apparatus and a colon polyp image processing apparatus. The endoscopic video stream may be transmitted between the endoscope apparatus and the colon polyp image processing apparatus in a wired or wireless manner. The endoscope apparatus may take images of the colon in a patient through the endoscope, to generate the endoscopic video stream. The colon polyp image processing apparatus detects the position of the polyp by using the polyp positioning model, so that the polyp image block may be directly positioned in the endoscopic image. The polyp type classification detection is also performed on the polyp image block, but does not need to be performed on the entire endoscopic image, so that the real-time performance meets requirements. When the endoscope is controlled to move, an identification result of an image acquired in real time may be outputted in real time, thereby improving processing efficiency of the polyp image.

Referring to FIG. 1-b, a colon polyp image processing method provided in an embodiment of this application may include the following steps.

In step 101, a colon polyp image processing apparatus detects a position of a polyp in a to-be-processed endoscopic image by using a polyp positioning model, and positions a polyp image block in the endoscopic image. The polyp image block includes a position region of the polyp in the endoscopic image.

In this embodiment of this application, the to-be-processed endoscopic image may be a single frame of endoscopic image obtained from the endoscopic video stream by the colon polyp image processing apparatus, or may be a single frame of endoscopic image received from an endoscope apparatus by the colon polyp image processing apparatus. After obtaining the single frame of endoscopic image, a position of a polyp position in the endoscopic image is detected by using a polyp positioning model trained in advance. The polyp positioning model includes network parameters that have been trained, and it may be detected, by using the network parameters of the polyp positioning model, which image regions in the endoscopic image meet polyp features, thereby determining the position region that meets the polyps features as the polyp image block circled in the endoscopic image in this embodiment of this application.

FIG. 7 is a schematic diagram of a polyp image block circled in an endoscopic image according to an embodiment of this application. The polyp image block includes the position region of the polyp in the endoscopic image. The completed polyp positioning model trained in advance is used in this embodiment of this application, and the polyp image block may be quickly circled through model detection, ensuring that the polyp image block may be determined in real time after the endoscopic video stream is generated, and ensuring that the polyp type classification detection may be performed in real time.

In some embodiments of this application, the endoscopic image may be classified as a white light type picture or an NBI type picture according to different picture types. Therefore, the polyp positioning model trained in advance also needs to be divided into a white light polyp positioning model and an NBI polyp positioning model. The white light polyp positioning model can be obtained in a manner that the colon polyp image processing apparatus performs polyp position training on the original polyp positioning model through white light type picture training data by using a neural network algorithm. The NBI polyp positioning model can be obtained in a manner that the colon polyp image processing apparatus performs polyp position training on the original polyp positioning model through NBI type picture training data by using the neural network algorithm.

In this embodiment of this application, first, training data for the white light type and the NBI type are obtained in advance, that is, the white light type picture training data and the NBI type picture training data are obtained. A polyp positioning model is obtained in advance through training using a neural network algorithm. The polyp positioning model may be trained by using a plurality of machine learning algorithms. For example, the polyp positioning model may be a deep neural network model, a cyclic neural network model or the like. For example, the polyp positioning model may be trained by using a YOLOv2 algorithm.

In some embodiments of this application, in an implementation scene where the polyp positioning model is divided into the white light polyp positioning model and the NBI polyp positioning model, the foregoing step 101 that a colon polyp image processing apparatus detects a position of a polyp in a to-be-processed endoscopic image by using a polyp positioning model, and positions a polyp image block in the endoscopic image can further include positioning the polyp by using the white light polyp positioning model in a case that the endoscopic image is the white light type picture, to position a white light polyp image block in the endoscopic image, and positioning the polyp by using the NBI polyp positioning model in a case that the endoscopic image is the NBI type picture, to position an NBI polyp image block in the endoscopic image.

In this embodiment of this application, it is necessary to determine the specific position of the polyp in the endoscopic image, to provide input data for the next operation of polyp property identification. Considering the requirements on real-time performance, in this embodiment of this application, the position of the polyp is detected by using the YOLOv2 algorithm. A principle and an implementation of YOLOv2 are described below. The YOLOv2 is a joint training method for detection and classification. A YOLO9000 model is trained based on a COCO detection data set and an ImageNet classification data set by using the joint training method, and the model can detect more than 9000 types of objects. YOLOv2 are improved in many aspects compared with YOLOv1, so that performance of YOLOv2 is remarkably improved, and the speed of YOLOv2 is still very fast. The YOLOv2 algorithm is an upgraded version of a YOLO algorithm, and is an end-to-end real-time target detection and recognition algorithm. By using a single neural network, the algorithm transforms a target detection problem into extraction of bounding boxes in images and a regression problem of category probabilities. Compared with YOLO, the YOLOv2 algorithm uses a multi-scale training method and borrows the concept of Faster RCNN anchor box, thus not only ensuring a detection speed, but also greatly improving the accuracy and generalization ability of model detection.

The YOLOv2 algorithm is applied to a polyp positioning task in this embodiment of this application, a detection target is a colon polyp, and a size of the anchor box is obtained through clustering according to built-in polyp training data. A transfer learning technology is used in algorithm training. Transfer learning refers to applying mature knowledge in a field to other scenes, and in terms of a neural network, it means transferring a weight of each node in network layers from a trained network to a brand new network instead of starting from scratch, and it is unnecessary to train a neural network for each specific task. Parameters trained by using an open-source, large-scale, labeled data set are used for initialization. For example, the data set may be Imagenet data. The Imagenet data is an open source data set related to image classification and target detection in the field of computer vision. The Imagenet data covers tens of thousands of categories, and has a data volume of more than one million. Using model initialization parameters trained by a large-scale data set may better allow a model to converge to a global optimal solution.

In an image classification model, white light type pictures and NBI type pictures may be distinguished. The two types of images differ greatly in terms of polyp appearances. A flow direction of a blood vessel may be observed in the NBI type picture, and the color of the blood vessel is black in the NBI type picture. Therefore, it is necessary to train respective polyp positioning models for the white light picture data and the NBI picture data, which are referred to as a white light polyp positioning model and an NBI polyp positioning model. The two polyp positioning models are both trained by using the method described above, and the only difference is training data of the models. The training data of the white light polyp positioning model is white light type pictures, and the training data of the NBI polyp positioning model is NBI type pictures. In a process of the algorithm, when a previous module determines an image as a white light type picture, the white light polyp positioning model is called to position the polyp; otherwise, the NBI polyp positioning model is called to position the polyp. The circled polyp image block is outputted in a case that the polyp is positioned, to be used as an input of a polyp property identification model.

Before the foregoing step 101, the colon polyp image processing method provided in this embodiment of this application may further include the following step 100. In step 100, the colon polyp image processing apparatus obtains the to-be-processed endoscopic image from an endoscopic video stream. In this embodiment of this application, when a doctor operates an endoscope to examine the colon, the endoscope apparatus may generate an endoscopic video stream, where the endoscopic video stream includes successive frames of endoscopic images. After the endoscope apparatus generates the endoscopic video stream, the endoscopic video stream may be transmitted to the colon polyp image processing apparatus. The colon polyp image processing apparatus may receive the endoscopic video stream from the endoscope apparatus, and obtain a single frame of endoscopic image from the endoscopic video stream. For each frame of endoscopic image, the polyp position and polyp type may be identified according to the method provided in this embodiment of this application, so that the property of the colon polyp in the endoscopic video stream may be identified in real time. When the doctor operates the endoscope to examine the colon, the position of the colon polyp in the video stream may be positioned in real time and the property of the polyp may be determined. If the polyp is identified as a non-adenomatous polyp, the doctor does not need to remove the polyp for pathological examination. Processing the endoscopic image of each frame according to this embodiment of this application may help the doctor to find the polyp in real time and prevent missed diagnosis of the polyp, and may also help the doctor to determine the property of the polyp, so that the doctor determines the polyp more accurately. In the subsequent steps, image processing may be performed on the endoscope image in the single frame to output an identification result. For the processing of endoscope images in other frames in the endoscopic video stream, refer to the foregoing processing procedure, which is only explained herein.

FIG. 2 is a schematic diagram of an endoscopic image according to an exemplary embodiment of this application. After the endoscopic video stream is generated, one frame of endoscopic image is extracted from the endoscopic video stream. In the picture shown in FIG. 2, the endoscopic image is a colon image shown in the box, parameters of the endoscope are shown on the left side of the endoscopic image, and parameter values of the endoscope may be set according to an actual scene. The parameters of the endoscope have nothing to do with the image processing. Therefore, only a colon image region may be reserved after the endoscopic video stream is acquired.

In algorithms designed in the related art, it is necessary to manually filter out low-quality noise data. However, the algorithms in the related art cannot be used in an actual production environment. Because the low-quality noise data is filtered out manually, the designed algorithms have a good effect in an ideal environment, but cannot be used in an actual scene. In order to resolve this problem, in some embodiments of this application, after step 100 of obtaining the to-be-processed endoscopic image from the endoscopic video stream, the method provided in this embodiment of this application further includes the following steps.

The colon polyp image processing apparatus extracts a color feature, a gradient variation feature and an abnormal brightness feature from the endoscopic image. Further, the colon polyp image processing apparatus can determine whether the endoscopic image is a low-quality picture according to the color feature, the gradient variation feature and the abnormal brightness feature, where the low-quality picture includes a blurred picture, an overexposed/underexposed picture with abnormal tone, and a low-resolution picture.

The following step 101 is triggered in a case that the endoscopic image is not the low-quality picture. The colon polyp image processing apparatus detects the position of the polyp position in the to-be-processed endoscopic image by using the polyp positioning model.

The low-quality picture may also be referred to as a low-quality picture. For the endoscopic image in a single frame in the input video stream, it is determined whether the endoscopic image is a low-quality picture; if the endoscopic image is the low-quality picture, the endoscopic image is directly filtered out and the subsequent module identification is skipped. In an actual production environment, there are a large number of blurred pictures and fecal water pictures caused by underprepared intestinal, which affect the subsequent polyp positioning and an algorithm effect of a property identification module. Therefore, in this embodiment of this application, the color feature, the gradient variation feature and the abnormal brightness feature may be extracted to detect, based on the three extracted features, whether the endoscopic image is the low-quality picture.

Figure 3:
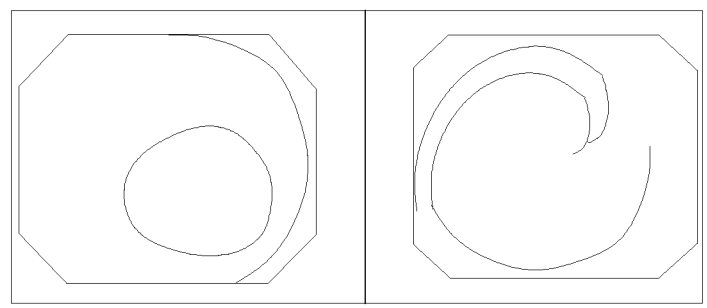
FIG. 3 is a schematic diagram of endoscopic images that are qualified pictures according to an embodiment of this application.
Figure 4:
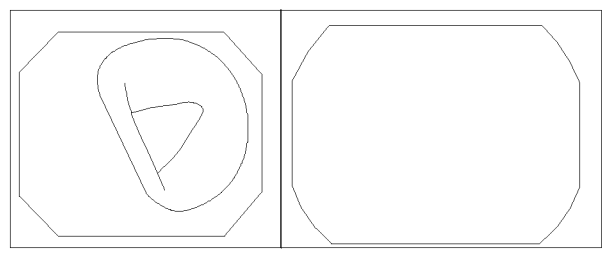
FIG. 4 is a schematic diagram of endoscopic images that are overexposed/underexposed pictures with abnormal tone according to an embodiment of this application.
Figure 5:
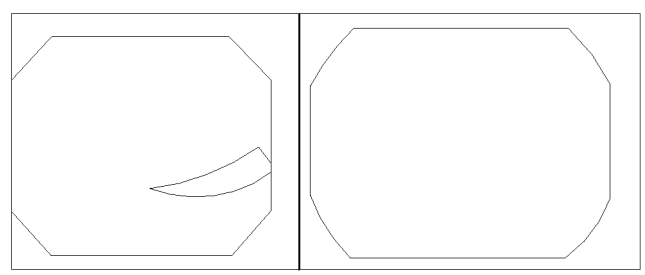
FIG. 5 is a schematic diagram of endoscopic images that are blurred pictures according to an embodiment of this application.

The low-quality picture defined in this embodiments of this application includes three categories blurred picture, overexposed/underexposed picture with abnormal tone, and low-resolution picture. FIG. 3 is a schematic diagram of endoscopic images that are a qualified pictures according to an embodiment of this application. The two pictures on the left and right shown in FIG. 3 are both qualified pictures. The qualified pictures refer to pictures other than the blurred picture, the overexposed/underexposed picture with abnormal tone, and the low-resolution picture. FIG. 4 is a schematic diagram of endoscopic images that are overexposed/underexposed pictures with abnormal tone according to an embodiment of this application. Abnormal colors occur in the both left and right pictures shown in FIG. 4, and therefore, the pictures are unqualified pictures. FIG. 5 is a schematic diagram of endoscopic images that are blurred pictures according to an embodiment of this application. Both the left and right pictures shown in FIG. 5 are blurred, and therefore are unqualified pictures. Specific identification processes of a blurred picture, an overexposed/underexposed picture with abnormal tone, and a low-resolution picture will be illustrated respectively below with examples.

Identification of a low-resolution picture may be achieved by calculating an effective pixel area in the picture. The effective pixel area refers to an area after black borders on upper, lower, left and right sides of the picture are removed through cropping, as shown by the area enclosed by a white box in FIG. 2. A black border cropping algorithm is mainly to collect statistics about gray-scale value distribution of pixel values in each row or each column. If a ratio of gray or black pixel values in a row or column is greater than a certain value, it is considered that the row or column needs to be removed through cropping. If the effective area after the black borders are removed through cropping is less than a certain threshold, the picture is considered to be a low-resolution picture, where the threshold may be customized according to actual applications.

A detection algorithm for a blurred picture can be performed as follows.

(1) A Gaussian filtering operation with a standard deviation sigma=2.5 is performed on an input image, to eliminate moiré generated in image sampling.

(2) An original image is defined as R, and an image P is obtained after a median filtering operation with a pixel value of 3*3 is performed.

(3) Gradients of the image P and image R are calculated respectively, and a gradient map G_P of the median filtered image and a gradient map G_R of the original image are obtained by using a Sobel edge detection operator. G_P and G_R highlight details of the image edges and enhance the image edges.

(4) A similarity between G_P and G_R is calculated. For example, a classification model estimation method, such as an algorithm similar to F-Score, may be used for screening. For a more blurred image, G_P and G_R have a higher similarity.

Finally, whether the endoscopic image is a blurred picture may be determined according to the similarity between G_P and G_R.

In a detection algorithm for an overexposed/underexposed picture with abnormal tone, there are numerous abnormal types, which can hardly be exhausted. Therefore, a standard library file for qualified tones and normal shooting is created. A detection algorithm can be performed as follows (1) An image is divided into 7*7 image blocks and nine image blocks are obtained.

(2) Hue (H), saturation (S), and value (V) of each image block are calculated in a Hue, Saturation, Value (HSV) space.

(3) H and S are used as features to match with H and S of a standard image respectively, a similarity threshold t is set, and it is calculated whether each image block of the image is similar to the standard library.

(4) Matching degree similarity results of the nine image blocks are accumulated, where a cumulative value is incremented by 1 when the matching degree is greater than the threshold t. When the cumulative value is greater than 5, the image is considered as a target tone matching image, and a returned detection result is True.

An endoscopic image that meets the foregoing target tone matching result may be determined as an overexposed/underexposed picture with abnormal tone.

In some embodiments of this application, the endoscopic video stream may be generated in a plurality of shooting methods. Therefore, the endoscopic images in the endoscopic video stream may include a plurality of picture types according to different shooting methods. Different polyp positioning models need to be used for different picture types during the polyp position detection, and details are described in the subsequent embodiments.

After step 100 of obtaining the to-be-processed endoscopic image from the endoscopic video stream, the method provided in this embodiment of this application further include that the colon polyp image processing apparatus identifies a picture type of the endoscopic image, and determines that the endoscopic image is a white light type picture or an NBI type picture.

According to different shooting methods used for the endoscopic video stream, the endoscopic image extracted from the endoscopic video stream may also have different picture types. For example, the endoscopic image may be a white light type picture or an NBI type picture. FIG. 6-a is a schematic diagram of an endoscopic image that is a white light type picture according to an embodiment of this application. The white light type picture refers to a red, green and blue (RGB) image that is imaged by an ordinary light source. FIG. 6-b is a schematic diagram of an endoscopic image that is an NBI type picture according to an embodiment of this application. In the NBI type picture, a broad band spectrum of RGB light waves emitted by the endoscope light source is removed by a filter, and only a narrow band spectrum is reserved for diagnosing various digestive tract diseases.

Further, in some embodiments of this application, the identifying a picture type of the endoscopic image, and determining that the endoscopic image is a white light type picture or an NBI type picture can include performing classification training on an original image classification model through white light type picture training data and NBI type picture training data by using a neural network algorithm, to obtain a trained image classification model. It can further include extracting a blood vessel color feature from the endoscopic image by using the trained image classification model, and classifying a value of the blood vessel color feature by using the trained image classification model, to obtain that the endoscopic image is the white light type picture or the NBI type picture.

In this embodiment of this application, first, training data for a white light type and an NBI type are obtained respectively, that is, white light type picture training data and NBI type picture training data are obtained. An image classification model is trained in advance by using a neural network algorithm, and the image classification model may be trained by using a plurality of machine learning algorithms. For example, the image classification model specifically may be a deep neural network (DNN) model, or a cyclic neural network model. For example, the deep neural network model may be densely connected convolutional networks (DenseNet). After the white light type picture training data and the NBI type picture training data are collected in advance model training is performed through the white light type picture training data and the NBI type picture training data, a trained image classification model is outputted.

After the training of the image classification model is completed, a blood vessel color feature is extracted from the endoscopic image by using the trained image classification model, and the blood vessels color feature is a basis for classification of the endoscopic image. Finally, a value of the blood vessels color feature is classified by using the trained image classification model to obtain that the endoscope image is the white light type picture or the NBI type picture.

In this embodiment of this application, an input of the image classification model is a qualified single frame of endoscopic image, and the image classification model outputs a result indicating whether the endoscopic image is a white light type picture or an NBI type picture. When a doctor actually operates an endoscope to examine the colon, if a suspected polyp is found, a pathological type of the current polyp is generally diagnosed in an NBI mode. A picture in the NBI mode may show a direction of the blood vessel more clearly. FIG. 6-a shows a white light type picture and FIG. 6-b shows an NBI type picture. For example, the image classification model in this embodiment of this application may classify and detect a picture type by using DenseNet. Certainly, other picture classification networks may also be used in this embodiment of this application to achieve similar functions; however, the identification effect may differ in some degree, which is not limited herein.

Execution of the image classification model may be converted into an image classification problem. An image classification algorithm used is the DenseNet. A size of an input image of the networks is 224*224. Therefore, an inputted original picture is scaled to a fixed size of 224*224 first. Considering that a task of the image classification model prefers lower-level feature combinations, for example, blood vessel color and the like, a wider and shallower mode is used when the combination of depth and width of the DenseNet structure is designed. The final network structure used is DenseNet-40, where 40 refers to the number of network layers. A growth-rate is set to 48 through network parameter optimization, and a compression ratio of features through a transition layer is 0.5, thereby achieving an optimal effect. A model structure is shown in the following Table 1.

| Layers | Output Size | Network layer settings (DenseNet-40) |
|---|---|---|
| Convolution | 112 × 112 | 7 × 7 conv, stride 2 |
| Pooling | 56 × 56 | 3 × 3 max pool, stride 2 |
| Dense Block (1) | 56 × 56 | $\begin{bmatrix} 1 \times 1\ conv \\ 3 \times 3\ conv \end{bmatrix} \times 6$ |
| Transition Layer (1) | 56 × 56 | 1 × 1 conv |
|  | 28 × 28 | 2 × 2 average pool, stride 2 |
| Dense Block (2) | 28 × 28 | $\begin{bmatrix} 1 \times 1\ conv \\ 3 \times 3\ conv \end{bmatrix} \times 6$ |
| Transition Layer (2) | 28 × 28 | 1 × 1 conv |
|  | 14 × 14 | 2 × 2 average pool, stride 2 |
| Dense Block (3) | 14 × 14 | $\begin{bmatrix} 1 \times 1\ conv \\ 3 \times 3\ conv \end{bmatrix} \times 6$ |
| Classification Layer | 1 × 1 | 7 × 7 global average pool 2D fully-connected, softmax classifier |

In the embodiment shown in the foregoing Table 1, the function implementation and execution process of each layer in DenseNet-40 may be determined according to scenes. In addition, cony in the network layers includes three operations: batch normalization (batchnorm), activation layer (ReLU) and a convolution layer.

In step 102, the colon polyp image processing apparatus can perform a polyp type classification detection on the polyp image block by using a polyp property identification model, and outputs an identification result. In this embodiment of this application, after the polyp image block is circled in the endoscopic image, next, it is only necessary to perform a polyp type classification detection on the polyp image block by using the polyp property identification model trained in advance, and output the identification result. The identification result may output a polyp type with a maximum probability, and may also output polyp types under various confidence conditions, where the confidence is a credibility of the polyp image block including various polyp types after a prediction is performed based on the polyp property identification model.

In this embodiment of this application, the polyp property identification model may perform a polyp property discrimination task, which is implemented, for example, through an image classification task, and an input is picture data of a positioning box outputted by the polyp positioning model. As shown in FIG. 7, the polyp image block circled in the endoscopic image is the polyp detected by the polyp positioning model, and is used as input data of the polyp property identification model. A module output may be four class values (0, 1, 2, 3), where 0 means that the region has no polyps and is normal, 1 represents a non-adenomatous polyp, 2 represents an adenomatous polyp, and 3 represents an adenocarcinoma. In addition, respective confidence conditions may be set for a normal region, a non-adenomatous, an adenomatous, and an adenocarcinoma. If the output is 0, a determining result of the polyp positioning model is corrected, this region has no polyps and is a normal region.

In some embodiments of this application, the step 102 where the colon polyp image processing apparatus performs a polyp type classification detection on the polyp image block by using a polyp property identification model, and outputs an identification result can include performing polyp type classification detection training on an original polyp property identification model through polyp picture training data of different polyp types by using a neural network algorithm, to obtain a trained polyp property identification model. The step 102 can further include extracting a polyp type feature from the polyp image block by using the trained polyp property identification model, and classifying a value of the polyp type feature by using the trained polyp property identification model, and outputting the identification result.

In this embodiment of this application, the polyp picture training data of different polyp types is obtained first. The polyp property identification model is obtained in advance through training using the neural network algorithm, and the polyp property identification model may be trained by using a plurality of machine learning algorithms. For example, the polyp property identification model may be a deep neural network model or a cyclic neural network model. For example, the deep neural network model may be DenseNet. After the polyp picture training data of different polyp types is collected in advance and model training is performed through the polyp picture training data of different polyp types, the trained polyp property identification model is outputted.

After the training of the polyp property identification model is completed, the polyp type feature is extracted from the polyp image block by using the trained polyp property identification model, and the polyp type feature is a basis for classification of the polyp image block. Finally, the value of the polyp type feature is classified by using the trained polyp property identification model, to obtain the identification result.

In some embodiments of this application, after step 102 that the colon polyp image processing apparatus positions the polyp image block in the endoscopic image, the method provided in this embodiment of this application further can include the following steps that the colon polyp image processing apparatus expands a polyp region occupied by the polyp image block in the endoscopic image upwards, downwards, leftwards and rightwards according to a preset image expansion ratio, to obtain an expanded polyp image block, and the colon polyp image processing apparatus inputs the expanded polyp image block into the polyp property identification model.

In this embodiment of this application, the polyp property classification task of the polyp property identification model may be implemented by using a DenseNet algorithm. The algorithm requires input images to have the same size. However, polyp positions outputted by the polyp positioning model has different sizes. During construction of algorithm input data, the method used in this embodiment of this application is as follows: for the polyp image block outputted by the polyp positioning model, expanding the region by 10% upwards, downwards, leftwards and rightwards to ensure the framed region has context semantic information, to help the subsequent polyp property identification model to extract features. The expanded region is directly normalized to an input size of 224*224 required by the model. Considering the complexity of the task, deeper DenseNet may be used. The final network structure used is DenseNet-121. A growth-rate is set to 24 through the network parameter optimization, and a compression ratio of features through a transition layer is 0.5, thereby achieving an optimal effect. A model structure is shown in the following Table 2.

| Layers | Output Size | Network layer settings (DenseNet-121) |
|---|---|---|
| Convolution | 112 × 112 | 7 × 7 conv, stride 2 |
| Pooling | 56 × 56 | 3 × 3 max pool, stride 2 |
| Dense Block (1) | 56 × 56 | $\begin{bmatrix} 1 \times 1\ conv \\ 3 \times 3\ conv \end{bmatrix} \times 6$ |
| Transition Layer (1) | 56 × 56 <br> 28 × 28 | 1 × 1 conv <br> 2 × 2 average pool, stride 2 |
| Dense Block (2) | 28 × 28 | $\begin{bmatrix} 1 \times 1\ conv \\ 3 \times 3\ conv \end{bmatrix} \times 12$ |
| Transition Layer (2) | 28 × 28 <br> 14 × 14 | 1 × 1 conv <br> 2 × 2 average pool, stride 2 |
| Dense Block (3) | 14 × 14 | $\begin{bmatrix} 1 \times 1\ conv \\ 3 \times 3\ conv \end{bmatrix} \times 24$ |
| Transition Layer (3) | 14 × 14 <br> 7 × 7 | 1 × 1 conv <br> 2 × 2 average pool, stride 2 |
| Dense Block (4) | 7 × 7 | $\begin{bmatrix} 1 \times 1\ conv \\ 3 \times 3\ conv \end{bmatrix} \times 16$ |
| Classification Layer | 1 × 1 | 7 × 7 global average pool <br> 2D fully-connected, softmax classifier |

Finally, according to the polyp image processing method provided in this embodiment of this application, it takes about 100 milliseconds (ms) to process each frame of endoscopic image, which meets requirements on real-time performance. Compared with doctors of different levels, the algorithm effect is equivalent to the level of top-notch doctors. When deployed in primary hospitals, the method may help doctors to find and identify polyps in real time.

In this embodiment of this application, the method may help a doctor to find a polyp and determine a property of the polyp in real time when the doctor conducts an endoscopic examination. The method may prevent the doctor from missing diagnosis of the polyp, and help the doctor to improve the accuracy of polyp property identification. If the polyp is identified a non-adenomatous polyp with high confidence, the doctor does not need to remove the polyp for pathological examination, which may reduce the operation time of the doctor, thereby further reducing a high complication risk of the patient and diagnosis cost of the patient, and reducing the burden of an endoscopist and a pathologist.

As can be learned from the description of the foregoing embodiments of this application, a position of a polyp in an endoscopic image is first detected by using a polyp positioning model, and a polyp image block is positioned in the endoscopic image, where the polyp image block includes: a position region of the polyp in the endoscopic image. Finally, a polyp type classification detection is performed on the polyp image block by using a polyp property identification model, and an identification result is outputted. In the embodiments of this application, because the position of the polyp is detected by using the polyp positioning model, the polyp image block may be directly positioned in the endoscopic image. The classification detection for the polyp type is also performed on the polyp image block, and does not need to be performed on the entire endoscopic image. Therefore, the real-time performance meets requirements. When the endoscope is controlled to move, an identification result of an image acquired in real time can be outputted in real time, thereby improving processing efficiency of the polyp image.

The foregoing method embodiments are expressed as a series of action combinations for the purpose of brief description, but it is to be learned by a person skilled in the art that, the embodiments of this application are not limited to the described action sequence because some steps may be performed in other sequences or simultaneously according to the exemplary embodiments of this application. In addition, it is to be also learned by a person skilled in the art that the embodiments described in this specification are all preferred embodiments, and the related actions and modules are not necessarily mandatory in the embodiments of this application.

For the convenience of better implementation of the foregoing solutions of the embodiments of this application, the following further provides a related apparatus configured to implement the foregoing solutions.

Referring to FIG. 8-*a*, an embodiment of this application provides a colon polyp image processing apparatus 800. The apparatus may include one or more processors and one or more memories storing a program unit, the program unit being executed by the processor. The program unit includes a position detection module 801 and a polyp classification module 802. Of course, it should be understood that one or more of the modules described in this specification may be implemented by processing circuitry.

The position detection module 801 is configured to detect a position of a polyp in a to-be-processed endoscopic image by using a polyp positioning model, and position a polyp image block in the endoscopic image, the polyp image block including a position region of the polyp in the endoscopic image.

The polyp classification module 802 is configured to perform a polyp type classification detection on the polyp image block by using a polyp property identification model, and output an identification result.

In some embodiments of this application, as shown in FIG. 8-*a*, the colon polyp image processing apparatus 800 may further include an image obtaining module 803. The image obtaining module 803 is configured to obtain the to-be-processed endoscopic image from an endoscopic video stream.

In some embodiments of this application, as shown in FIG. 8-*b*, the colon polyp image processing apparatus 800 can further include a low-quality picture identification module 804, configured to extract a color feature, a gradient variation feature and an abnormal brightness feature from the endoscopic image before the position detection module 801 detects the position of the polyp in the to-be-processed endoscopic image by using the polyp positioning model, determine whether the endoscopic image is a low-quality picture according to the color feature, the gradient variation feature and the abnormal brightness feature. The low-quality picture includes a blurred picture, an overexposed/underexposed picture with abnormal tone, and a low-resolution picture, and trigger the position detection module in a case that the endoscopic image is not the low-quality picture.

In some embodiments of this application, referring to FIG. 8-*c*, the colon polyp image processing apparatus 800 further includes a picture type identification module 805, configured to identify a picture type of the endoscopic image before the position detection module 801 detects the position of the polyp in the to-be-processed endoscopic image by using the polyp positioning model, and determine that the endoscopic image is a white light type picture or an endoscope NBI type picture.

In some embodiments of this application, referring to FIG. 8-*d*, the picture type identification module 805 includes an image classification model training unit 8051, configured to perform classification training on an original image classification model through white light type picture training data and NBI type picture training data by using a neural network algorithm, to obtain a trained image classification model. The picture type identification module 805 can further include a blood vessel color feature extraction unit 8052, configured to extract a blood vessel color feature from the endoscopic image by using the trained image classification model to, and a picture classification unit 8053, configured to classify a value of the blood vessel color feature by using the trained image classification model, to obtain that the endoscopic image is the white light type picture or the NBI type picture.

In some embodiments of this application, the polyp positioning model includes a white light polyp positioning model and an NBI polyp positioning model. Further, the white light polyp positioning model is obtained in the following manner: the colon polyp image processing apparatus performs polyp position training on the original polyp positioning model through the white light type picture training data by using the neural network algorithm. Additionally, the NBI polyp positioning model can be obtained by the colon polyp image processing apparatus perform polyp position training on the original polyp positioning model through the NBI type picture training data by using the neural network algorithm.

In some embodiments of this application, the position detection module 801 is specifically configured to perform polyp positioning by using the white light polyp positioning model in a case that the endoscopic image is the white light type picture, to position a white light polyp image block in the endoscopic image, and perform polyp positioning by using the NBI polyp positioning model in a case that the endoscopic image is the NBI type picture, to position an NBI polyp image block in the endoscopic image.

In some embodiments of this application, referring to FIG. 8-*e*, the polyp classification module 802 includes a polyp property identification model training unit 8021 that is configured to perform polyp type classification detection training on an original polyp property identification model through polyp picture training data of different polyp types by using a neural network algorithm, to obtain a trained polyp property identification model. The polyp classification module 802 can further include a polyp type feature extraction unit 8022 that is configured to extract a polyp type feature from the polyp image block by using the trained polyp property identification model, and a polyp classification unit 8023 that is configured to classify a value of the polyp type feature by using the trained polyp property identification model, and output the identification result.

As can be learned from the description of the foregoing embodiments of this application, a position of a polyp in an endoscopic image is first detected by using a polyp positioning model, and a polyp image block is positioned in the endoscopic image, where the polyp image block includes a position region of the polyp in the endoscopic image. Finally, a polyp type classification detection is performed on the polyp image block by using a polyp property identification model, and an identification result is outputted. In the embodiments of this application, because the position of the polyp is detected by using the polyp positioning model, the polyp image block may be directly positioned in the endoscopic image. The classification detection for the polyp type is also performed on the polyp image block, and does not need to be performed on the entire endoscopic image. Therefore, the real-time performance meets requirements. When the endoscope is controlled to move, an identification result of an image acquired in real time can be outputted in real time, thereby improving processing efficiency of the polyp image.

An exemplary embodiment of this application further provides another terminal. As shown in FIG. 9, for ease of description, only parts related to the embodiments of this application are shown. For specific technical details that are not disclosed, refer to the method part in the embodiments of this application. The terminal may be any terminal device including a mobile phone, a tablet computer, a personal digital assistant (PDA), a point of sales (POS), an on-board computer and the like, and the terminal being a mobile phone is used as an example.

FIG. 9 is a block diagram of a partial structure of a mobile phone related to a terminal according to an embodiment of this application. Referring to FIG. 9, the mobile phone includes components such as a radio frequency (RF) circuit 1010, a memory 1020, an input unit 1030, a display unit 1040, a sensor 1050, an audio circuit 1060, a Wi-Fi module 1070, a processor 1080, and a power supply 1090. A person skilled in the art may understand that the structure of the mobile phone shown in FIG. 9 does not constitute a limitation to the mobile phone, and the mobile phone may include more components or fewer components than those shown in the figure, or some components may be combined, or a different component deployment may be used.

The components of the mobile phone are described in detail below with reference to FIG. 9. The RF circuit 1010 may be configured to receive and transmit signals during an information receiving and transmitting process or a call process. Specifically, the RF circuit receives downlink information from a base station, then delivers the downlink information to the processor 1080 for processing, and transmits designed uplink data to the base station. Usually, the RF circuit 1010 includes, but is not limited to, an antenna, at least one amplifier, a transceiver, a coupler, a low noise amplifier (LNA), and a duplexer. In addition, the RF circuit 1010 may also communicate with a network and another device through wireless communication. The wireless communication may use any communications standard or protocol, including, but not limited to a global system of mobile communication (GSM), a general packet radio service (GPRS), code division multiple access (CDMA), wideband code division multiple access (WCDMA), Long Term Evolution (LTE), an email, a short messaging service (SMS), and the like.

The memory 1020 may be configured to store a software program and module. The processor 1080 runs the software program and module stored in the memory 1020, to implement various functional applications of the mobile phone and data processing. The memory 1020 may mainly include a program storage area and a data storage area. The program storage area may store an operating system, an application program required for at least one function, such as an audio playing function, an image playing function, and the like. The data storage area may store data, such as audio data, a phone book, and the like, created according to use of the mobile phone. In addition, the memory 1020 may include a high speed random access memory, and may further include a non-volatile memory, such as at least one magnetic disk memory device, a flash memory device, or other non-volatile solid state memory devices.

The input unit 1030 may be configured to receive an entered numeral or character information, and generate key signal input related to user setting and function control of the mobile phone. Specifically, the input unit 1030 may include a touch panel 1031 and other input devices 1032. The touch panel 1031, also referred to as a touchscreen, may collect a touch operation performed by a user on or near the touch panel, such as an operation performed by a user on the touch panel 1031 or near the touch panel 1031 by using any proper object or accessory, such as a finger or a stylus. The touch panel can further drive a corresponding connecting apparatus according to a preset program. Optionally, the touch panel 1031 may include two parts, a touch detection apparatus and a touch controller. The touch detection apparatus detects a touch position of a user, detects a signal generated by the touch operation, and transfers the signal to the touch controller. The touch controller receives the touch information from the touch detection apparatus, converts the touch information into touch point coordinates, and transmits the touch point coordinates to the processor 1080. Moreover, the touch controller can receive and execute a command sent from the processor 1080. In addition, the touch panel 1031 may be a touch panel of a resistive, capacitive, infrared, or surface acoustic wave type. In addition to the touch panel 1031, the input unit 1030 may further include another input device 1032. Specifically, the another input device 1032 may include, but is not limited to, one or more of a physical keyboard, a function key including a volume control key or a power on/off key, a trackball, a mouse, a joystick, and the like.

The display unit 1040 may be configured to display information entered by a user or information provided for the user, and various menus of the mobile phone. The display unit 1040 may include a display panel 1041. Optionally, the display panel 1041 may be configured by using a liquid crystal display (LCD), an organic light-emitting diode (OLED), and the like. Further, the touch panel 1031 may cover the display panel 1041. After detecting a touch operation on or near the touch panel 1031, the touch panel 1031 transfers the touch operation to the processor 1080, to determine a type of a touch event. Then, the processor 1080 provides a corresponding visual output on the display panel 1041 according to the type of the touch event. Although, in FIG. 9, the touch panel 1031 and the display panel 1041 are used as two separate parts to implement input and output functions of the mobile phone, in some embodiments, the touch panel 1031 and the display panel 1041 may be integrated to implement the input and output functions of the mobile phone.

The mobile phone may further include at least one sensor 1050 such as an optical sensor, a motion sensor, and other sensors. Specifically, the optical sensor may include an ambient light sensor and a proximity sensor. The ambient light sensor may adjust luminance of the display panel 1041 according to brightness of the ambient light. The proximity sensor may switch off the display panel 1041 and/or backlight when the mobile phone is moved to the ear. As one type of motion sensor, an acceleration sensor can detect magnitude of accelerations in various directions generally on three axes, may detect magnitude and a direction of the gravity when static, and may be applied to an application that recognizes the attitude of the mobile phone, for example, switching between landscape orientation and portrait orientation, a related game, and magnetometer attitude calibration, a function related to vibration recognition, such as a pedometer and a knock, and the like. Other sensors, such as a gyroscope, a barometer, a hygrometer, a thermometer, and an infrared sensor, which may be configured in the mobile phone, are not further described herein.

The audio circuit 1060, a speaker 1061, and a microphone 1062 may provide audio interfaces between the user and the mobile phone. The audio circuit 1060 may convert received audio data into an electrical signal and transmit the electrical signal to the speaker 1061. The speaker 1061 converts the electrical signal into a sound signal for output. On the other hand, the microphone 1062 converts a collected sound signal into an electrical signal. The audio circuit 1060 receives the electrical signal, converts the electrical signal into audio data, and outputs the audio data to the processor 1080 for processing. Then, the processor 1080 transmits the audio data to, for example, another mobile phone by using the RF circuit 1010, or outputs the audio data to the memory 1020 for further processing.

Wi-Fi belongs to a short distance wireless transmission technology. The mobile phone may help, by using the Wi-Fi module 1070, a user to receive and send an email, browse a web page, access stream media, and the like. This provides wireless broadband Internet access for the user. Although FIG. 9 shows the Wi-Fi module 1070, it may be understood that the Wi-Fi module 1070 is not a necessary component of the mobile phone, and when required, the Wi-Fi module 1070 may be omitted without changing the scope of the essence of the present disclosure.

As a control center of the mobile phone, the processor 1080 is connected to all parts of the entire mobile phone by using various interfaces and lines, and performs various functions and data processing of the mobile phone by running or executing the software program and/or module stored in the memory 1020 and invoking the data stored in the memory 1020, to perform overall monitoring on the mobile phone. Optionally, the processor 1080 may include one or more processing units. Preferably, the processor 1080 may integrate an application processor and a modem. The application processor mainly processes an operating system, a user interface, and an application program and the like, and the modem mainly processes wireless communication. It may be understood that the foregoing modem may alternatively not be integrated into the processor 1080.

The mobile phone further includes the power supply 1090 (such as a battery) for supplying power to the components. Preferably, the power supply may be logically connected to the processor 1080 by using a power management system, thereby implementing functions such as charging, discharging, and power consumption management by using the power management system. Although not shown in the figure, the mobile phone may further include a camera, a Bluetooth module, and the like, which are not described herein.

In an embodiment of this application, the processor 1080 included in the terminal further controls and performs a procedure of a colon polyp image processing method performed by the terminal.

Figure 10:
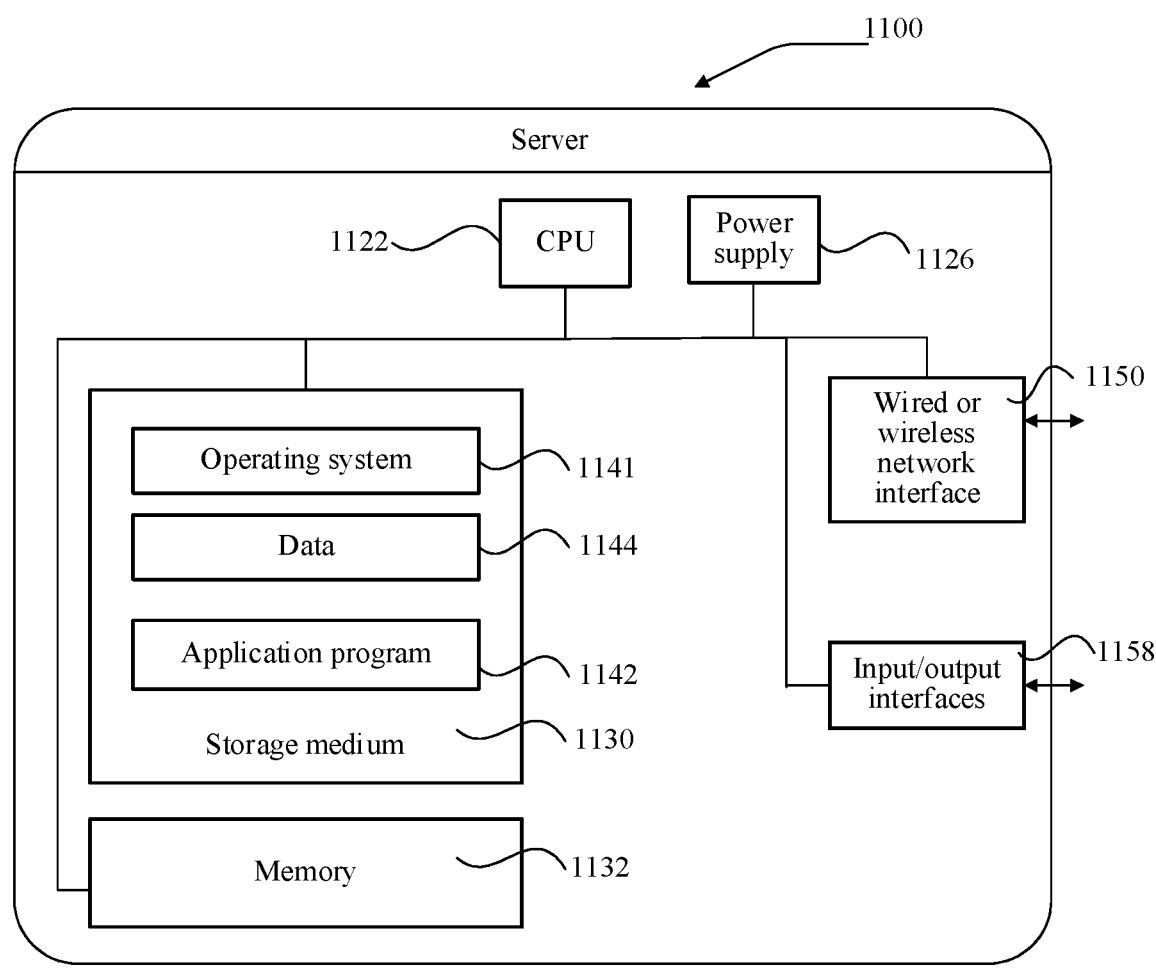
FIG. 10 is a schematic structural diagram of compositions of a server to which a colon polyp image processing method is applied according to an embodiment of this application.

FIG. 10 is a schematic structural diagram of a server according to an exemplary embodiment of this application. The server 1100 may vary greatly due to different configurations or performance, and may include one or more central processing units (CPU) 1122, for example, one or more processor, and a memory 1132, and one or more storage medium 1130, for example, one or more mass storage devices, that store application programs 1142 or data 1144. The memory 1132 and the storage medium 1130 may be transient storage or non-transitory permanent storage. The program stored in the storage medium 1130 may include one or more modules (not shown), and each module may include a series of instructions and operations for the server. Further, the CPU 1122 may be set to communicate with the storage medium 1130, and perform, on the server 1100, the series of instruction operations in the storage medium 1130.

The server 1100 may further include one or more power supplies 1126, one or more wired or wireless network interfaces 1150, one or more input/output interfaces 1158, and/or one or more operating systems 1141, for example, Windows Server™, Mac OS X™, Unix™, Linux™, or FreeBSD™.

The steps of the colon polyp image processing method performed by the server in the foregoing embodiment may be based on the server structure shown in FIG. 10.

In addition, the described apparatus embodiment is merely an example. The units described as separate parts may or may not be physically separate, and parts displayed as units may or may not be physical units, may be located in one position, or may be distributed on a plurality of network units. Some or all of the units may be selected according to actual needs to achieve the objectives of the solutions of the embodiments. Besides, in the accompanying drawings of the apparatus embodiments of this application, a connection relationship between modules indicates a communication connection between them, and can be specifically implemented as one or more communications buses or signal lines. A person of ordinary skill in the art may understand and implement the embodiments of this application.

According to the descriptions in the foregoing implementations, a person skilled in the art may clearly understand that the embodiments of this application may be implemented by software and necessary general hardware, and certainly can also be implemented by specific hardware including an application-specific integrated circuit, a specific CPU, a specific memory, a specific component, and the like. Generally, any function implemented by a computer program can be easily implemented by corresponding hardware, and specific hardware structures for implementing the same function may be various. The structures may be an analog circuit, a digital circuit, a specific circuit, or the like. However, for the embodiments of this application, the implementation by a software program is the better one in more cases. Based on such an understanding, the technical solutions in the embodiments of this application essentially or the part contributing to the related art may be implemented in a form of a software product. The computer software product is stored in a non-transitory computer readable storage medium, such as a floppy disk of a computer, a USB flash drive, a removable hard disk, a read-only memory (ROM), a random access memory (RAM), a magnetic disk, or an optical disc and includes several instructions for instructing a computer device, which may be a personal computer, a server, a network device, or the like, to perform the method described in the embodiments of this application.

In summary, the foregoing exemplary embodiments are merely intended for describing the technical solutions of the embodiments of this application, but not for limiting this application. Although the embodiments of this application are described in detail with reference to the foregoing embodiments, it is to be understood by a person of ordinary skill in the art that they may still make modifications to the technical solutions described in the foregoing embodiments or make equivalent replacements to some technical features thereof, without departing from the spirit and scope of the technical solutions of the embodiments of this application.

In an embodiment of this application, a position of a polyp in an endoscopic image is first detected by using a polyp positioning model, and a polyp image block is positioned in the endoscopic image, where the polyp image block includes a position region of the polyp in the endoscopic image. Finally, a polyp type classification detection is performed on the polyp image block by using a polyp property identification model, and an identification result is outputted. In the embodiments of this application, because the position of the polyp is detected by using the polyp positioning model, the polyp image block may be directly positioned in the endoscopic image. The classification detection for the polyp type is also performed on the polyp image block, and does not need to be performed on the entire endoscopic image. Therefore, the real-time performance meets requirements. When the endoscope is controlled to move, an identification result of an image acquired in real time can be outputted in real time, thereby improving processing efficiency of the polyp image.

What is claimed is:

1. A colon polyp image processing method, comprising:
   identifying, by an image classification model, a picture type of an endoscopic image based on a blood vessel color feature of the endoscopic image;
   detecting, by processing circuitry of a colon polyp image processing apparatus, a position of a polyp in the endoscopic image by using a polyp positioning model based on the identified picture type;
   positioning a polyp image block in the endoscopic image, the polyp image block being a subregion in the endoscopic image; and
   performing a polyp type classification detection on the subregion in the endoscopic image of the polyp image block by using a polyp property identification model, and outputting an identification result.

2. The method according to claim 1, wherein, before the detecting, the method further comprises:
   extracting at least one of a color feature, a gradient variation feature, or an abnormal brightness feature from the endoscopic image;
   determining whether the endoscopic image is a low-quality picture according to the at least one of the color feature, the gradient variation feature, or the abnormal brightness feature, wherein the low-quality picture is one of a blurred picture, an overexposed/underexposed picture with abnormal tone, and a low-resolution picture; and
   triggering a detecting of the position of the polyp in the endoscopic image by using the polyp positioning model when the endoscopic image is not the low-quality picture.

3. The method according to claim 1, wherein the identifying comprises:
   identifying the picture type of the endoscopic image as a white light type picture or an endoscope narrow band imaging (NBI) type picture.

4. The method according to claim 3, wherein
   the image classification model is a trained image classification model; and
   the identifying further comprises:
   performing classification training on an original image classification model through white light type picture training data and NBI type picture training data by using a neural network algorithm to obtain the trained image classification model;
   extracting the blood vessel color feature from the endoscopic image by using the trained image classification model; and
   classifying a value of the blood vessel color feature by using the trained image classification model to determine that the endoscopic image is the white light type picture or the NBI type picture.

5. The method according to claim 3, the polyp positioning model comprising a white light polyp positioning model and an NBI polyp positioning model, wherein:
   the white light polyp positioning model is obtained by the colon polyp image processing apparatus performing polyp position training on an original polyp positioning model through white light type picture training data by using a neural network algorithm, and
   the NBI polyp positioning model is obtained by the colon polyp image processing apparatus performing polyp position training on the original polyp positioning model through NBI type picture training data by using the neural network algorithm.

6. The method according to claim 5, wherein the detecting further comprises:
   performing polyp positioning by using the white light polyp positioning model when the endoscopic image is the white light type picture to position a white light polyp image block in the endoscopic image; and
   performing polyp positioning by using the NBI polyp positioning model when the endoscopic image is the NBI type picture to position an NBI polyp image block in the endoscopic image.

7. The method according to claim 1, wherein the performing further comprises:
   performing polyp type classification detection training on an original polyp property identification model through polyp picture training data of different polyp types by using a neural network algorithm to obtain a trained polyp property identification model;
   extracting a polyp type feature from the polyp image block by using the trained polyp property identification model; and
   classifying a va lue of the polyp type feature by using the trained polyp property identification model and outputting the identification result.

8. The method according to claim 7, wherein, after the positioning the polyp image block in the endoscopic image, the method further comprising:
   expanding a polyp region occupied by the polyp image block on the endoscopic image upwards, downwards, leftwards, and rightwards according to a preset image expansion ratio to obtain an expanded polyp image block; and
   inputting the expanded polyp image block into the polyp property identification model.

9. A colon polyp image processing apparatus, comprising:
   processing circuitry configured to:
   identify, by an image classification model, a picture type of an endoscopic image based on a blood vessel color feature of the endoscopic image;
   detect a position of a polyp in the endoscopic image by using a polyp positioning model based on the identified picture type;
   position a polyp image block in the endoscopic image, the polyp image block being a subregion in the endoscopic image; and
   perform a polyp type classification detection on the subregion in the endoscopic image of the polyp image block by using a polyp property identification model and output an identification result.

10. The apparatus according to claim 9, wherein the processing circuitry is further configured to:
    extract at least one of a color feature, a gradient variation feature, or an abnormal brightness feature from the endoscopic image before the position of the polyp in the endoscopic image is detected by using the polyp positioning model;
    determine whether the endoscopic image is a low-quality picture according to the at least one of the color feature, the gradient variation feature, or the abnormal brightness feature, wherein the low-quality picture is one of a blurred picture, an overexposed/underexposed picture with abnormal tone, and a low-resolution picture; and
trigger the detection of the position when the endoscopic image is not the low-quality picture.

11. The apparatus according to claim 9, wherein the processing circuitry is further configured to:
identify the picture type of the endoscopic image as a white light type picture or an endoscope narrow band imaging (NBI) type picture.

12. The apparatus according to claim 11, wherein
the image classification model is a trained image classification model; and
the processing circuitry is further configured to:
perform classification training on an original image classification model through white light type picture training data and NBI type picture training data by using a neural network algorithm to obtain the trained image classification model;
extract the blood vessel color feature from the endoscopic image by using the trained image classification model; and
classify a value of the blood vessel color feature by using the trained image classification model to determine that the endoscopic image is the white light type picture or the NBI type picture.

13. The a ppa ratus according to claim 11, the polyp positioning model including a white light polyp positioning model and an NBI polyp positioning model, wherein:
the white light polyp positioning model is obtained by performing polyp position training on an original polyp positioning model through white light type picture training data by using a neural network algorithm, and
the NBI polyp positioning model is obtained by performing polyp position training on the original polyp positioning model through NBI type picture training data by using the neural network algorithm.

14. The a ppa ratus according to claim 13, wherein the processing circuitry is further configured to:
perform polyp positioning by using the white light polyp positioning model when the endoscopic image is the white light type picture to position a white light polyp image block in the endoscopic image; and
perform polyp positioning by using the NBI polyp positioning model when the endoscopic image is the NBI type picture to position an NBI polyp image block in the endoscopic image.

15. A medical system, comprising an endoscope apparatus, a colon polyp image processing apparatus, and a communication connection between the endoscope apparatus and the colon polyp image processing a ppa ratus, wherein:
the endoscope apparatus is configured to generate an endoscopic video stream and transmit the generated endoscopic video stream to the colon polyp image processing apparatus, and
the colon polyp image processing apparatus is configured to receive the endoscopic video stream from the endoscope apparatus, obtain the endoscopic image from the endoscopic video stream, and perform the method according to claim 1.

16. An image processing method, comprising:
identifying, by an image classification model, a picture type of an image based on a blood vessel color feature of the image;
detecting, by an image processing apparatus, a position of a target object in the image by using a target object positioning model based on the identified picture type;
positioning a target object image block in the image, the target object image block being a subregion in the image; and
performing a target object type classification detection on the subregion in the image of the target object image block by using a target object property identification model and outputting an identification result.

17. The method according to claim 16, wherein, before the detecting, the method further comprises:
extracting at least one of a color feature, a gradient variation feature, or a n abnormal brightness feature from the image;
determining whether the image is a low-quality picture according to the at least one of the color feature, the gradient variation feature, or the abnormal brightness feature, wherein the low-quality picture is one of a blurred picture, an overexposed/underexposed picture with abnormal tone, and a low-resolution picture; and
triggering, when the image is not the low-quality picture, the performing the target object position detection on the image by using the target object positioning model.

18. The method according to claim 16, wherein the identifying further comprises:
identifying the picture type of the image as a white light type picture or an endoscope narrow band imaging (NBI)type picture.

19. The method according to claim 18, wherein
the image classification model is a trained image classification model; and
the identifying further comprises:
performing classification training on a n original image classification model through white light type picture training data and NBI type picture training data by using a neural network algorithm to obtain the trained image classification model;
extracting the color feature of a specified object from the image by using the trained image classification model; and
classifying a value of the color feature of the specified object by using the trained image classification model to determine that the image is the white light type picture or the NBI type picture.

20. The method according to claim 18, wherein the target object positioning model comprises a white light target object positioning model and a n NBI target object positioning model, wherein:
the white light target object positioning model is obtained by the image processing apparatus performing target object position training on an original target object positioning model through white light type picture training data by using a neural network algorithm; and
the NBI target object positioning model is obtained by the image processing apparatus performing target object position training on the original to rget object positioning model through NBI type picture training data by using the neural network algorithm.

* * * * *